United States Patent [19]

Davila et al.

[11] Patent Number: 5,894,018
[45] Date of Patent: Apr. 13, 1999

[54] VACCINE COMPOSITION COMPRISING AUTOLOGOUS EPIDERMAL GROWTH FACTOR OR A FRAGMENT OR A DERIVATIVE THEREOF HAVING ANTI-TUMOR ACTIVITY AND USE THEREOF IN THE THERAPY OF MALIGNANT DISEASES

[75] Inventors: Augustin Bienvenido Lage Davila; Gisela Gonzalez Marinello; Belinda Sanchez Ramirez; Eduardo Suarez Peztana; Irene Beausoleil Delgado; Gilda Nurez Gandolf, all of Habana, Cuba

[73] Assignee: Centro De Immunologia Molecular, Havana, Cuba

[21] Appl. No.: 08/604,332

[22] Filed: Feb. 21, 1996

Related U.S. Application Data

[63] Continuation-in-part of application No. 08/353,551, Dec. 9, 1994, abandoned.

[30] Foreign Application Priority Data

Dec. 9, 1993 [CU] Cuba ............................ 113/93

[51] Int. Cl.$^6$ ........................ A61K 39/00; A61K 39/385; A61K 39/40; A61K 39/395
[52] U.S. Cl. .................... 424/195.11; 424/184.1; 424/198.1; 424/130.1; 424/158.1; 514/12; 530/350
[58] Field of Search ............... 424/130.1, 184.1, 424/195.11, 198.1; 530/350; 514/12

[56] References Cited

U.S. PATENT DOCUMENTS

| | | |
|---|---|---|
| 4,717,717 | 1/1988 | Zinkenaur . |
| 4,877,611 | 10/1989 | Cantrell . |
| 5,102,663 | 4/1992 | Livingston et al. . |
| 5,158,935 | 10/1992 | Nascimento et al. . |
| 5,229,289 | 7/1993 | Kjeldsen et al. . |
| 5,334,379 | 8/1994 | Pillai et al. . |
| 5,397,770 | 3/1995 | Levin et al. . |
| 5,468,494 | 11/1995 | Gevas et al. . |
| 5,571,894 | 11/1996 | Wels et al. . |
| 5,578,482 | 11/1996 | Lippman et al. . |
| 5,730,977 | 3/1998 | Ooka et al. . |

OTHER PUBLICATIONS

R.P. Rodriquez et al.: Los factores de crecimiento y sus relaciones con la transformacion maligna; *Interferon y Biotecnologia*, 3:179–209 (1986).

M.A. Rios et al.: Receptors for Epidermal Growth Factor and Estrogen as Predictors of Relpase in Patients with Mammary Carcinoma; *Anticancer Research*, 8:173–176 (1988).

Stoscheck, C.M. et al.: Role of Epidermal Growth Factor in Carcinogenesis; *Cancer Research*, 46:1030–1037 (1986).

Aaronson, S.A.: Growth Factors and Cancer; *Science*, 254:1146–1153 (1991).

Rusch, V. et al.: Differential Expression of the Epidermal Growth Factor Receptor and Its; Ligands in Primary Non–Small Cell Lung Cancers and Adjacent Benign Lung *Cancer Research*, 53:2379–2385 (1993).

Dassonville, O.: Expression of Epidermal Growth Factor Receptor and Survival in Upper Aerodigestive Tract Cancer; *Journal of Clinical Oncology*, 11:1873–1878 (1993).

Janinis, J. et al.: Immunohistochemical expression of EFG-R in malignant surface epithelial ovarian neoplasms (SEON); *Eur. J. Gynaec. Oncol.*, pp. 19–23 (1994).

Perez, R. et al.: Epidermal growth factor receptors in human breast cancer; *Breast Cancer Research and Treatment*, 4:189–193 (1984).

Klijn et al.: The prognostic value of epidermal growth factor receptor (EGF-R) in primary breast cancer: Results of a 10 year follow-up study; *Breast Cancer Research and Treatment*, 29:73–83 (1994).

Ichiyoshi et al.: Epidermal Growth Factor in Gastric Carcinoma as a Risk Factor of Postoperative Recurrence; *Int. Surg.*, 78:196–199 (1993).

Masui, H. et al.; Growth Inhibition of Human Tumor Cells in Athymic Mice by Anti–Epidermal Growth Factor Receptor Monoclonal Antibodies; *Cancer Research*, 44:1002–1007 (1984).

Rodeck, U.: Tumor GRowth Modulation by a Monoclonal Antibody to the Epidermal Growth Factor Receptor: Immunologically Mediated and Effector Cell–independent Effects; *Cancer Research*, 47:3692–3696 (1987).

Divgi et al.: Phase I and Imaging Trial of Indium 111–Labeled Anti–Epidermal Growth Factor Receptor Monoclonal Antibody 225 in Patients With Squamous Cell Lung Carcinoma; *Articles*, 82:97–104 (1991).

Brady, L.W. et al.: Iodine–125–Labeled Anti–Epidermal Growth Factor Receptor–425 in the Treatment of Glioblastoma Multiforme; *Front. Radiol. Ther. Oncol*, 24:151–160 (1990).

LeMaistre, C.F. et al.: Targeting the EGF receptor in breast cancer treatment; *Breast Cancer Research and Treatment*, 32:97–103 (1994).

Gonzalez et al., Vaccine Research, Jun. 2:91–100, 1997.

Bixler et al., Synthetic Vaccines vol. 1 Editor: Amon pp. 39–71, 1987.

(List continued on next page.)

*Primary Examiner*—Nita Minnifield

[57] ABSTRACT

The invention provides novel uses of EGF and vaccine compositions comprising EGF. In particular, autologous EGF, or a fragment or a derivative thereof, is used as an active immunization against the proliferation of EGF-dependent tumors, or other EGF-dependent diseases. Autologous EGF is preferably coupled to a carrier protein, such as tetanus toxoid or Cholera toxin B chain. The vaccine compositions according to the invention will usually comprise an adjuvant such as aluminum hydroxide.

15 Claims, 15 Drawing Sheets

OTHER PUBLICATIONS

Article entitled: Epidermal Growth Factor Receptors in Human Breast Cancer. Authors: Rolando Perez, Maria Pascual, Amparo Macias, Agustin Lage. Published in Breast Cancer Research and Treatment, 4, 189–193 (1984).

Article entitled: Receptors for Epidermal Growth Factor in Human Mammary Carcinomas and their Matastases. Authors: Amparo Macias, Edward Azavedo, Rolando Perez, Lars Erik Rutqvist and Lambert Skoog –Published in Anticancer Research 7: 849–852 (1986).

Article entitled: Epidermal Growth Factor Inhibits Thymidine Incorporation in Enrlich Ascites Tumor Cells in Vivo. Authors: J. Lombardero, R. Perez, A. Lage –Published in Neoplasma, 33, 4, 1986.

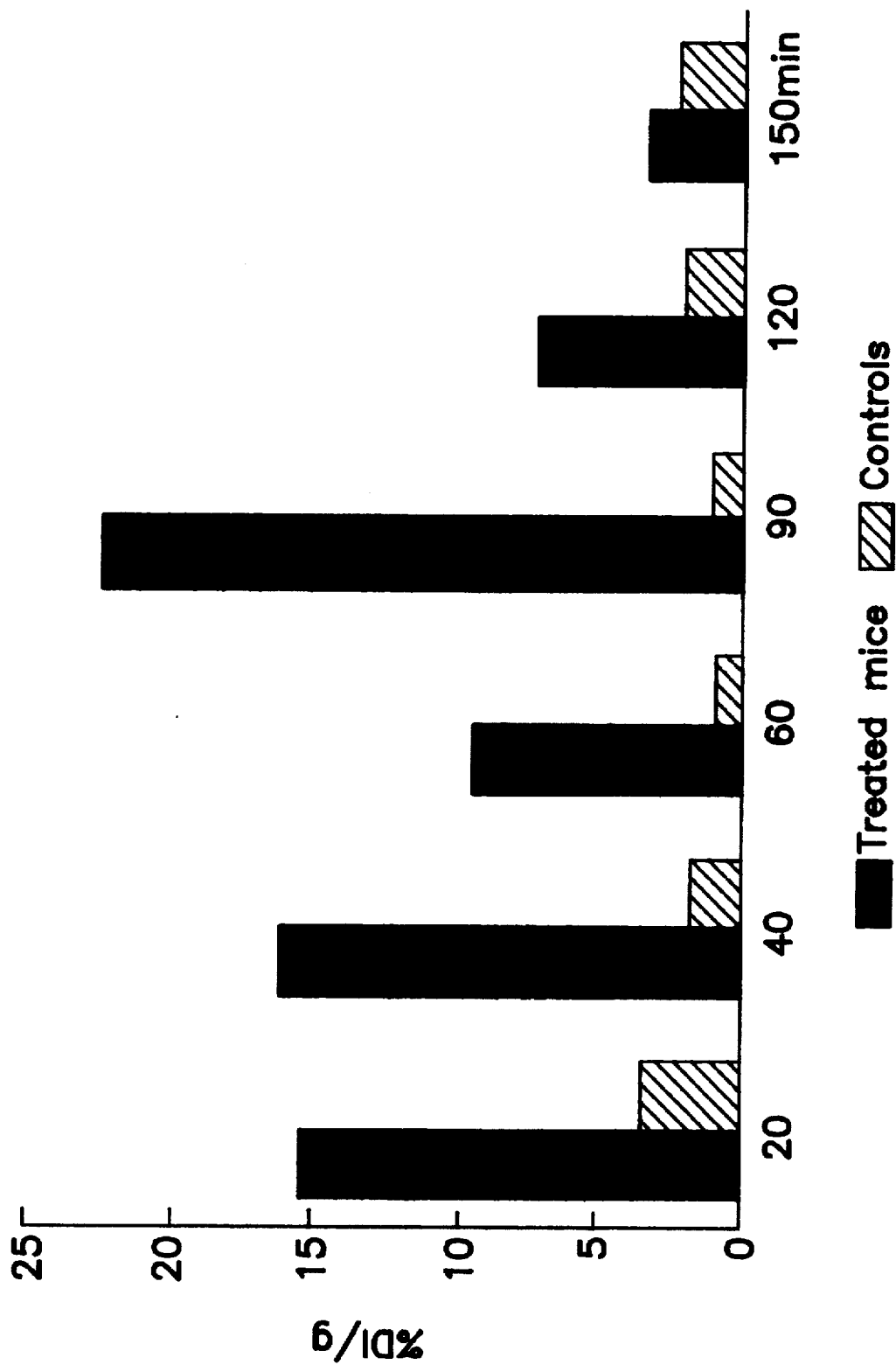

VACCINE COMPOSITION COMPRISING AUTOLOGOUS EPIDERMAL GROWTH FACTOR OR A FRAGMENT OR A DERIVATIVE THEREOF HAVING ANTI-TUMOR ACTIVITY AND USE THEREOF IN THE THERAPY OF MALIGNANT DISEASES

This application is a continuation-in-part of application Ser. No. 08/353,551 filed on Dec. 9, 1994, now abandoned

FIELD OF THE INVENTION

This invention relates to the field of immunology, in particular to vaccine compositions able to produce an autoimmune reaction against autologous (self) Epidermal Growth Factor (EGF).

An important object of this invention is to obtain a vaccine composition for the active immunotherapy of EGF dependent malignant tumors (e.g. epidermoid carcinoma of lung, glioblastoma multiforme and head and neck epidermoid carcinomas), which can inhibit the proliferation of those tumors, and which therefore are useful for the treatment of malignant neoplasms and of other EGF related diseases. Thus, the invention is also related to the field of cancer therapy.

DESCRIPTION OF THE PRIOR ART

Epidermal Growth Factor, a polypeptide that stimulates epithelial cell proliferation, has been considered to be one of the growth factors involved in malignant transformations. Its action is mainly performed via its membrane receptors.

Epidermal Growth Factor (EGF) is a 53 amino acid polypeptide, its molecular weight is about 6,045 D. It was isolated and purified for the first time from the murine submaxillary gland (Cohen S. J.Biol Chem (1962) 237, 1.555). Later a similar molecule was obtained from human urine (Cohen S. Human Epidermal Growth factor: Isolation and Chemical and Biological Properties PNAS USA 72,1975 1 317).

EGF is capable of stimulating the proliferation of epithelial and mesenchymal cells, both in vitro and in vivo (Cohen S., Carpenter G., PNAS USA 72, 1317, 1975) and EGF gives a specific stimulation in some breast cancer cell lines (Osborne C. K. et al. Can Res. 40.2.361 (1980). A role of the EGF in the differentiation process of the mammary gland, mainly for the development of the lobule alveolar system has been demonstrated (Tonelli C. J. Nature (1980) 285, 250–252).

This bio-regulating action is exerted via a membrane receptor (EGF-R), a 1,186 amino acid glycoprotein of about 170 kD, the gene of which has been cloned and sequenced. The intracellular domain of the receptor is associated with an activity of Tyrosine specific protein kinase which shows a structural homology to the oncogene product v-erb-B showing the relation to the malignant transformation process (Heldin C. H. Cell 37, 9–20 (1984)).

EGF and its receptor constitute a molecular complex of high specificity and the interaction between them develops important mechanisms of cell growth regulation.

High levels of EGF-R have been detected in malignant tumors of epithelial origin, such as breast, bladder, ovarian, vulva, colonic, pulmonary, brain and oesophagus cancers. The role played by EGF and its receptor in regulating tumor growth is unknown, but there are suggestions that the EGF-R expression in tumor cells provides a mechanism for autocrine growth stimulation which leads to uncontrolled proliferation (Schlessinger J., Schreiber A. B., Levi A., Liberman T., Yarden Y. Crit. Rev. Biochem. 1983, 14 (2) 93–111).

The presence of EGF-R in tumor cells has proven to be an indication of a poor prognosis in human breast cancer. Approximately 40% of the breast tumors show specific binding sites of high affinity for EGF. There is also an inverse correlation with the presence of oestrogen receptor indicating EGF-R as a dedifferentiation marker or an indicator of the potential capacity of proliferation of the malignant cells (Perez R., Pascual M. R., Macias A., Lage A., Breast Cancer Research and Treatment 4, 189–193, 1984).

It also has been reported that the EGF-R expression is higher in regional ganglional metastases than in the primary breast carcinomas (Sainsbury J. R., et al. (1985): Lancet 1 (8.425), 364–366), and that the expression of the receptor is different in the different histologic subtypes of breast carcinomas cells, which also makes their presence a signal of bad prognosis (Macias A., et al. (1986); Anticancer Res.6: 849–852).

Previous studies performed in the Ehrlich Ascitic Tumor (EAT) model in Balb-C mouse, demonstrated the in vivo inhibitory effect of EGF (Lombardero J., et al. Neoplasma 33, 4 (1987), suggesting the possibility of considering this molecule as a biological response modifier.

The presence of an EGF precursor molecule has been previously reported in the cell membrane of EGF dependent tumors. The present inventors have reported it to be an important fact to consider this molecule as a target for the action of auto-antibodies.(Patent Application Cuba No. 113/93).

The results obtained in different studies, have prompted the consideration of the EGF/EGF-R system as a possible target for therapeutic actions.

Passive immunotherapy using monoclonal antibodies against the EGF-R, has been the object of multiple investigations, which have demonstrated that the specific recognition by the the antibody of the receptor inhibits the EGF binding, with an inhibitory effect on the mitogenic stimulation of malignant cells (SATO J. D., et al. Methods in Enzymology, vol. 146 pp 63–81, 1987), however; these antibodies which are of murine origin will usually produce a human anti mouse antibody response (HAMA).

Until the present invention, no active immunotherapy against EGF dependent tumors capable of inhibiting proliferation has been proposed, since the art consistently reports that "self" molecules will not induce any immune reaction because the host has been educated to be tolerant to self.

The present invention provides a vaccine composition containing autologous EGF coupled to a carrier protein, which complex will inhibit the EGF dependent tumors' growth, through an autoimmune effect, without the collateral effects of the introduction of a heterologous protein in the human body.

This vaccine composition can be used in the treatment of EGF dependent tumors or any malignant disease associated to EGF.

It will be understood that in this specification EGF is to be read as including any fragment and/or derivative of EGF which has similar immunological properties and/or effects as the original molecule. Derivatives include, but are not limited to, conventional amino acid substitutions, site-directed replacement of amino acids for enhanced stability and/or activity, chemical modifications and the like.

DETAILED DESCRIPTION OF THE INVENTION

I. OBTAINING AN IMMUNOGENIC PREPARATION

Several preparations were obtained, some based on murine EGF (mu-EGF) coupled to carrier proteins, others on human recombinant EGF (hu-rec-EGF) (National Medicament Register Office from Cuba, HEBERMIN, No.1266) coupled to carrier proteins (including monoclonal antibodies). The compositions were always administered through the parenteral route, subcutaneously.

The preparations containing mu-EGF conjugated to carrier proteins (such as Cholera toxin B chain and recombinant P64 as an example of an outer membrane protein from *Neisseria meningitidis*) were used in studies performed in mice as a model to determine the immunogenicity and the antitumoral effect of a vaccine preparation containing an autologous EGF molecule.

The preparations containing hu-rec-EGF coupled to carrier proteins were used in studies in non-human primates to determine their immunogenicity in a species more closely related to humans, as a necessary step preceding clinical use of the proposed vaccine preparations. A proper adjuvant was applied.

Immunogenicity studies were performed in primates with the conjugate hu-rec-EGF/carrier protein [−] since the human EGF is very similar to the primate EGF though it is recognized as a self molecule. These results allowed demonstration of the immunogenic response an autologous molecule can elicit.

To obtain the preparations, a solution of murine or hu-rec-EGF in PBS/MgCl$_2$ 10 mM, is mixed with a solution of the carrier protein in the same solvent, in a ratio of between 1 and 5 moles of EGF per mol of protein.

Afterwards glutaraldehyde 0.5% is added to obtain a final concentration between 0.1% and 0.05%.

The mixture is incubated between 1 and 3 hours at room temperature and subsequently dialyzed in PBS/Mgcl$_2$ 10 mM with, at least, 3 changes of dialysis solution.

CONJUGATE CHARACTERIZATION

The test of the conjugation efficiency and of the maintenance of the antigenicity is performed through an ELISA assay.

ELISA plates of activated PVC (NUNC) were coated with 50 µl of an antiserum against the carrier protein utilized, in a concentration between 1 and 10 µg/ml. In the case of cholera toxin chain B (CTB) as carrier, the plates were coated with the ganglioside GMI.

Subsequently 3 washes with PBS/Tween were carried out; then the plates were blocked with a solution of BSA between 0.5 and 1% in PBS/Tween, and then incubated during a period of 30 minutes to 1 hour at 37° C. Dilutions between 0.1 and 0.001 mg/ml of the conjugates to be assayed were added to the plates, 50 µl/well, and incubated for 1 to 2 hours at 37° C.

In the next step a mouse anti hu-rec-EGF antiserum was added in a dilution between 1:500 and 1:1000, 50 µl/well, and incubated for between 30 minutes and 1 hour at 37° C.

As the last step, the plates were incubated with an anti-mouse-alkaline phosphatase antiserum, in a dilution between 1:500 and 1:1000, 50 µl/well, for 30 minutes to 1 hour at 37° C.

Reaction color was developed with p-nitrophenylphosphate, at a concentration of 1 mg/ml in diethanolamine, 50 µl/well, incubated for 30 minutes at 37° C. Optical density was measured at 405 nm in an ELISA plate reader.

The results demonstrated the activity of the molecule and the efficiency of the conjugation, because the conjugate maintains its recognition site for the molecule coating the plates, which specifically recognizes the carrier protein and, at the same time can be recognized by an anti EGF antiserum.

II. CHARACTERIZATION OF EFFECTS PRODUCED BY THE PREPARATION CONTAINING mu-EGF. PRE-CLINICAL STUDIES

IIa) ENDOGENOUS EGF IMMUNOGENICITY: INDUCTION OF AUTO-IMMUNITY IN MICE

In order to demonstrate the capacity of the immunogenic preparation containing mu-EGF obtained through the technique described in item I of inducing autoimmunity against the endogenous EGF, a test was performed in Balb/C mice.

Groups of animals were inoculated each week for 4 to 6 weeks with different doses in the range of 50 to 100 µg of mu-EGF conjugated to a carrier protein, per animal.

In the first week the immunogenic preparation was prepared in a ratio of 1:1 with complete Freund's adjuvant; all the following doses were prepared with incomplete Freund's adjuvant.

The same procedure was performed in a control group, but only adjuvant was administered to the animals. One week after the last immunization, blood was extracted from the animals, the serum separated from the remainder of the blood and the titer of antibodies against mu-EGF was determined by an ELISA technique.

IIb) IMMUNOGENICITY OF hu-rec-EGF

In order to demonstrate the immunogenicity of hu-rec-EGF in mice and to show that the antibodies against hu-rec-EGF recognize the mu-EGF, the experiment was performed in Balb/C mice.

Groups of animals were inoculated each week for 4 to 6 weeks with different doses in the range of 50 to 100 µg of hu-rec EGF-protein per animal.

In the first week the immunogenic preparation was prepared in a ratio of 1:1 with complete Freund's adjuvant; all the following doses were prepared with incomplete Freund's adjuvant.

The same procedure is performed in a control group, but only adjuvant is administered to the animals.

One week after the last immunization, blood was extracted from the animals, the serum was separated from the rest of the blood and the titer of antibodies against mu-EGF was determined by an ELISA technique.

IIc) ANTITUMOR ACTIVITY

The main objective of this experimental procedure is to determine whether the immune response obtained against the autologous EGF is able to elicit any antitumor effect in EGF dependent tumors.

The animals with higher antibody titer, determined according to the technique described previously, were inoculated with Ehrlich Ascitic Tumor (EAT) in cellular concentrations between 0.2 to 2 million cells per animal. The control group was treated in the same manner.

The animals were observed for grafting as well as for survival.

III. CHARACTERIZATION OF THE IMMUNE RESPONSE

IIIa) ISOTYPE OF THE ANTIBODY RESPONSE

In order to determine whether the autoimmune response obtained upon the immunization of mice with the autologous EGF is a response producing antibodies of the isotype IgM or IgG, an ELISA assay was performed testing the sera of immunized animals with EGF according to the techniques described in items II a) and b). In the case of IgM characterization an antiserum against this molecule was incubated with the samples. IgG characterization is performed with an antiserum against IgG.

IIIb) CHARACTERIZATION OF THE MEMORY OF THE IMMUNE RESPONSE

The development of a product to be used as a vaccine in an active therapy requires the determination of its capability of inducing an immunological memory and the determination of the duration of said memory if it is induced.

This information allows the possibility of a correct design of the immunization schemes that can be implemented with the product.

Groups of mice are immunized with one dose between 50 and 100 µg of hu-rec-EGF per animal in complete Freund's adjuvant in a proportion 1:1.

The kinetics of antibody production against mu-EGF was studied in different groups of animals. This study was performed after the first immunization and after the reimmunizations when the titer is declining. The antibody levels are determined using an ELISA technique.

IV. IMMUNOGENICITY STUDIES IN NON HUMAN PRIMATES

The criteria of immunogenicity of the immunogenic preparations to be used in humans are based on results obtained in non human primates because these are the species that are the closest to human.

A group of Rhesus monkeys (Macaca mulatta) are immunized with the immunogenic preparation containing hu-rec-EGF in a dose of 50 µg (conjugated with tetanic toxoid) and together with the adjuvant. After the last immunization blood samples were extracted and antibody titers against hu-rec-EGF were determined. This experiment provides information about the immunogenicity of the preparation of hu-rec-EGF coupled to tetanic toxoid and demonstrates that the response obtained is long lasting.

A group of Chimpanzees (Pan troglodytes) were immunized with hu-rec-EGF coupled to monoclonal antibodies as carrier proteins, in 4 doses of 50 µg of conjugated EGF, and together with adjuvant. After the last immunization, a blood sample was extracted and antibody titers against hu-rec-EGF were determined. This experiment provides information about whether the tested monoclonal antibodies could be used as carrier proteins in an EGF vaccine.

A group of Green monkeys (Cercopithecus aethiops) were immunized with hu-rec-EGF coupled to tetanic toxoid and to IOR-T3 monoclonal antibody in an immunization scheme of 2 doses of 50 µg of conjugated EGF adsorbed into Al(OH)$_3$ as adjuvant. After the last immunization a sample was extracted and antibody titers against hu-rec-EGF were determined. In this experiment we tested whether the immunization protocol proposed for use in clinical trials could induce antibody titers against the hu-rec-EGF contained in the tested vaccine preparations.

EXPERIMENTS

EXAMPLE 1
STUDY OF THE PRESENCE OF AN EGF PRECURSOR MOLECULE IN THE CELL MEMBRANE OF EGF DEPENDENT TUMORS

This study was performed through a Western Blotting technique. Samples of 5 ductal carcinomas of the breast in different stages, one head and neck tumor, four samples of fibrocystic dysplasia and five normal samples obtained as controls were studied.

Cell membranes were obtained from the samples through the procedure described elsewhere (Grimaux M., Rev. Neurol. 1988, 144: 101–103).

Electrophoresis was performed at 250 V, 10 mA, at 15° C. Molecular weight standards were used in the range of 14,300 D (Lysozyme) to 340,000 D (alpha 2 macroglobulin).

Proteins separated during electrophoresis were transferred to a nitrocellulose membrane of 0.45 µm in a Phast system equipment in a buffer transfer solution. After the transfer the membrane was blocked overnight with 10% skimmed milk with constant stirring.

After three washes in buffer solution a mouse monoclonal antibody recognizing human EGF was added and incubated during one hour.

After three washes a biotinylated anti-mouse antibody was added and incubated during one hour. Peroxidase streptavidine conjugate was added and reaction developed with diaminobenzidine and hydrogen peroxide after one hour of incubation.

The results obtained demonstrated that the samples studied corresponding to normal tissues did not show any band in the zone of high molecular weight according to the standards. However, the samples corresponding to breast pathology (dysplasia and carcinomas) showed a diffuse banding in the high molecular weight zone. This is an experimental evidence of the presence of a high MW EGF precursor in the tumor membranes.

EXAMPLE 2
OBTAINING THE mu-EGF/CTB CONJUGATE

One ml of mu-EGF in PBS/MgCl$_2$ 10 mM at a concentration of 1 mg/ml, was mixed with 2 ml of a solution of CTB in the same solvent at a ratio of 1 mol of mu-EGF per mol of CTB. Glutar-aldehyde (3 ml, 0.5%) was added to obtain a final concentration of 0.05%.

Incubation was performed during 1 hour at room temperature and subsequently dialyzed in PBS/MgCl$_2$ 10 mM with, at least, 3 changes of the dialysis solution.

EXAMPLE 3
mu-EGF/CTB CONJUGATED CHARACTERIZATION

ELISA assay for conjugate test: PVC activated ELISA plates (NUNC) were coated with 50 µl of the GM1 ganglioside (recognizing the CTB molecule) in a concentration of 4 µg/ml in methanol, which was left to dry off in the flow during 1 hour.

Subsequently 3 washes with PBS/Tween were carried out and then the plates were blocked with a solution of BSA 1% in PBS/Tween and incubated during 30 minutes at 37° C.

Conjugated dilutions between 0.1 and 0.001 mg/ml were added to the plates at 50 µl/well and incubated during 1 hour at 37° C.

Next a mouse anti-mu-EGF antiserum in a 1:1000 dilution, 50 µl/well was added and incubated for 1 hour at 37° C.

Then, the plates were incubated with anti-mouse antiserum alkaline phosphatase conjugate (dilution 1:1000), 50 µl/well for 1 hour at 37° C. The color was developed with p-nitrophenylphosphate at a concentration of 1 mg/ml in diethanolamine, 50 µl/well, incubated for 30 minutes at 37° C. optical density was measured at 405 nm.

The results demonstrated a direct relationship between the concentration of the conjugate and the absorbance values. This demonstrates the activity of the conjugate and the efficiency of the conjugation, since the molecule maintains the recognition for the GM1 ganglioside (identifies CTB) and, at the same time, is recognized by an anti mu-EGF antiserum (FIG. 1).

EXAMPLE 4
IMMUNOGENICITY OF AUTOLOGOUS EGF: INDUCTION OF AUTO-IMMUNITY IN MICE

In order to demonstrate that the immunogenic preparation containing autologous EGF is capable of inducing autoimmunity, experiments were performed in Balb/c mice.

Groups of animals were inoculated subcutaneously each week for 4 to 6 weeks with doses of 50 µg of conjugated mu-EGF per animal.

In the first week the immunogenic preparation was prepared in a proportion 1:1 with complete Freund's adjuvant; all the following doses were prepared with incomplete Freund's adjuvant.

The same procedure was performed in a control group, but only adjuvant was administered to the animals. One week after the last immunization, blood was extracted from the animals, the serum obtained and the titer of antibodies against mu-EGF was determined by an ELISA technique.

Costar plates were coated with mu-EGF at a concentration of 10 µg/ml in carbonate bicarbonate buffer (pH 9.6), and incubated overnight. After the plates were washed the samples were added in different dilutions. Incubation took place during one hour. Alkaline phosphatase anti-mouse antibody conjugate was added and incubated during one hour after which color was developed and optical density measured at 405 nm in an ELISA reader.

All the animals immunized with the mu-EGF-CTB preparation developed antibody titer against the mu-EGF up to 1:1000 dilution. The control group did not show any antibody titer (FIG. 2).

EXAMPLE 5
IMMUNOGENICITY OF hu-rec-EGF: INDUCTION OF AUTO-IMMUNITY IN MICE

In order to demonstrate that the immunogenic preparation containing hu-rec-EGF was capable of producing antibody titer against mu-EGF, experiments were performed in Balb/c mice.

Groups of animals were inoculated with doses of 50 µg of hu-rec-EGF per animal subcutaneously, each week for 4 to 6 weeks.

In the first week the immunogenic preparation was prepared in a proportion 1:1 with complete Freund's adjuvant; all the following doses were prepared with incomplete Freund's adjuvant.

The same procedure was performed in a control group, but only adjuvant was administered to the animals.

One week after the last immunization, blood was extracted from the animals, the serum obtained and the titer of antibodies against mu-EGF was determined by an ELISA technique.

Costar plates were coated with mu-EGF at a concentration of 10 µg/ml in carbonate bicarbonate buffer (pH 9.6), and incubated overnight. After the plates were washed the samples were added in different dilutions. Incubation took place during one hour. The alkaline phosphatase anti-mouse antibody conjugate was added and incubated during one hour after which color was developed and optical density measured at 405 nm in an ELISA reader.

All the animals immunized with the hu-rec-EGF preparation developed antibody titer against the mu-EGF up to 1:20000 dilution.

The control group did not show any antibody titer (FIG. 3).

EXAMPLE 6
IMMUNOGENICITY OF hu-rec EGF IN A PREPARATION WITH ALUMINUM HYDROXIDE In order to demonstrate that the immunogenic preparation containing hu-rec-EGF and aluminium hydroxide as adjuvant was capable of producing antibody titer against mu-EGF, experiments were performed in Balb/c mice.

Groups of animals were inoculated with doses of 50 µg of hu-rec-EGF (with aluminum hydroxide as adjuvant) per animal subcutaneously, each week for 4 to 6 weeks.

The same procedure was performed in a control group, but only adjuvant was administered to the animals. One week after the last immunization, blood was extracted from the animals, the serum obtained and the titer of antibodies against mu-EGF was determined by an ELISA technique.

Costar plates were coated with mu-EGF at a concentration of 10 µg/ml in carbonate bicarbonate buffer (pH 9.6), and incubated overnight. After the plates were washed the samples were added in different dilutions. Incubation took place during one hour. The alkaline phosphatase anti-mouse antibody conjugate was added and incubated during one hour, after which color was developed and optical density measured at 405 nm in an ELISA reader.

All the animals immunized with the hu-rec-EGF/ aluminium hydroxide preparation developed antibody titer against the mu-EGF up to 1:4000 dilution.

The control group did not show any antibody titer (FIG. 4).

EXAMPLE 7
ANTI-TUMOR ACTIVITY

The main objective of this experimental procedure was to determine whether the immune response obtained against the autologous EGF was able to elicit any antitumor effect in EGF dependent tumors.

The immunized animals with higher antibody titer, determined according to the technique described previously in example 5, were inoculated with Ehrlich Ascitic Tumor (EAT) in cellular concentrations of 2 million cells EAT per animal. The control group (non-immunized mice) was treated in the same manner.

The animals were observed for grafting as well as for survival. Survival curves of treated and control animals are shown in FIG. 5.

The Increase in Life Span Index was 22.5% showing an increase in survival for the treated animals in relation to the control statistically significant according to the Mantel Haenszel and Wilcoxon tests.

EXAMPLE 8
ASSOCIATION BETWEEN ANTIBODY TITER AGAINST mu-EGF AND $^{125}$I EGF BIODISTRIBUTION

This experiment was performed to demonstrate that there is a different biodistribution of 125I EGF in animals with antibody titer against mu-EGF in relation to animals that did not have antibody titer against mu-EGF.

An experiment with 4 groups of mice was performed for this purpose:

Group 1: 30 mice with antibody titer against mu-EGF.

Group 2: 30 mice without antibody titer against mu-EGF.

Group 3: 30 mice with antibody titer against mu-EGF grafted with EAT.

Group 4: 30 mice without antibody titer against mu-EGF grafted with EAT.

Samples from group 1 and 2 were taken from blood, lung, kidneys, liver and skin at the following times: 2, 5, 8, 11, 15, 20, 30, 60, 120 and 150 minutes and 3 animals were sacrificed at every corresponding time, counting the radio-activity in the organs extracted.

The results obtained have shown a difference in the accumulation of $^{125}$I-EGF in time mainly in kidney and liver (FIG. 6a,b), indicating that the presence of antibodies against EGF alters the biodistribution of this molecule.

Samples from group 3 and 4 were taken from blood, lung, kidneys, liver, skin and from the ascitic fluid at the following times: 2, 5, 8, 11, 15, 20, 30, 60, 120 and 150 minutes and 3 animals were sacrificed at every corresponding time, and the radioactivity counted in the organs extracted.

Less accumulation of the labelled EGF was observed in the ascitic fluid of animals with antibody titer than in the animals without antibody titer (FIG. 7), indicating a more rapid depuration of the EGF present in the ascitic fluid in these animals and/or a limitation in EGF access to the ascites.

EXAMPLE 9
IMMUNE RESPONSE CHARACTERIZATION: ISOTYPE OBTAINED AGAINST AUTOLOGOUS EGF

In order to know whether the autoimmune response obtained upon the immunization of mice with the autologous EGF was a response producing antibodies of the isotype IgM or IgG, an ELISA assay was performed in which the plates were coated with EGF to a concentration of 10 µg/ml, 50 µg/well, and incubated for 1 hour at 37° C.

Subsequently, dilutions between 1:10 and 1:1000 of the sera of animals immunized with mu-EGF-CTB according to Example 5 were applied, 50 µg/well, and were incubated for 1 hour at 37° C.

A parallel design of microtiter plates was applied to measure IgG or IgM response with the corresponding antiserum (anti-IgG or anti-IgM respectively).

Color in the plates was developed with p-nitrophenyl phosphate, at a concentration of 1 mg/ml in diethanolamine, incubating during 30 minutes at 37° C and values of optical density at 405 nm were read.

IgG response was obtained in all treated animals (FIG. 8).

EXAMPLE 10
CHARACTERIZATION OF THE MEMORY OF THE IMMUNE RESPONSE AGAINST AUTOLOGOUS EGF

Two groups of 10 mice were studied with a single immunization of 50 µg hu-re-EGF in complete Freund's adjuvant. Group I.—The kinetics of antibody production against mu-EGF was studied in this group of animals. Every 4 days blood samples were extracted. The antibody levels were determined by an ELISA technique. Group II.—This group consisted of animals immunized at the same time as animals of Group I. These animals were re-immunized when antibody titers were declining (as was known by the determination of titers in Group I), and then every 2 days blood samples were extracted. The antibody levels were determined by an ELISA technique.

Results have shown a memory response when the animals were re-immunized with the preparation, after the decrease in the antibody titers developed with the first immunization (FIG. 9).

EXAMPLE 11
OBTENTION OF THE IMMUNOGENIC PREPARATION: hu-rec-EGF/TETANIC TOXOID A solution of hu-rec-EGF in PBS/MgCl$_2$ 10 mM at a concentration of 1.4 mg/ml, was mixed with 2 ml of a solution of TT in the same solvent at a concentration of 4 mg/ml. Glutaraldehyde (3 ml, 0.5%) was added to obtain a final concentration of 0.05%.

Incubation was performed during 1 hour at room temperature and subsequently dialysed in PBS/MgCl$_2$ 10 mM with, at least, 3 changes of the dialysis solution.

EXAMPLE 12
CONJUGATE CHARACTERIZATION: hu-rec-EGF/TETANIC TOXOID ELISA assay for conjugate test Costar plates (High Binding) were coated with 50 µl of an anti-TT antiserum obtained in sheep, in a concentration of 10 µg/ml and incubating it overnight.

Subsequently 3 washes with PBS/Tween were carried out and then the plates were blocked with a solution of BSA 1% in PBS/Tween, and incubated during 30 minutes at 37° C.

Conjugate dilutions between 0.1 and 0.001 mg/ml were added to the plates at 50 µl/well, and incubated during 1 hour at 37° C.

Next a mouse anti-hu-rec-EGF antiserum in a 1:1000 dilution, 50 µl/well was added, and incubated for 1 hour at 37° C.

Then, the plates were incubated with anti-mouse antiserum alkaline phosphatase conjugate (dilution 1:1000), 50 µl/well for 1 hour at 37° C. The color was developed with p-nitrophenylphosphate at a concentration of 1 mg/ml in diethanolamine, 50 µl/well, incubated for 30 minutes at 37° C, and optical density was measured at 405 nm.

The results demonstrated a direct relationship between the concentration of the conjugate and the absorbance values.

This demonstrates the activity of the conjugate and the efficiency of the conjugation, since the molecule maintains the recognition for anti-TT antiserum and, at the same time, is recognized by an anti-mu-EGF antiserum (FIG. 10).

EXAMPLE 13
STUDY OF THE IMMUNOGENICITY OF hu-rec-EGF COUPLED TO A CARRIER PROTEIN (TT) IN NON-HUMAN PRIMATES The study was performed with 4 Rhesus monkeys (*Macaca mulatta*), being submitted to a clinical veterinary examination including:

Physical examination,

Thorax X rays,

Blood tests.

These animals were immunized with a hu-rec-EGF coupled to TT, according to Example 10.

Immunization was performed subcutaneously in weeks 1, 2, 3, 4, 6 and 12. Complete Freund's adjuvant was used in the first immunization and incomplete Freund's adjuvant in all others.

Blood was extracted from the animals and antibody titers were determined through an ELISA.

Costar plates were coated with hu-rec-EGF at a concentration of 10 µg/ml in carbonate bicarbonate buffer (pH 9.6), and incubated overnight. After the plates were washed the samples were added in different dilutions. Incubation took place during one hour. The alkaline phosphatase anti-human antibody conjugate was added and incubated during one hour after which color was developed and optical density measured at 405 nm in an ELISA reader.

All the animals immunized with the hu-EGF-TT preparation developed antibody titer against the hu-EGF up to 1:200000 dilution (FIG. 11). A long lasting immune response was observed.

EXAMPLE 14
STUDY OF P64 PROTEIN AS CARRIER MOLECULE IN EGF VACCINE, INDUCTION OF AUTOIMMUNITY IN MICE

Recombinant P64 (membrane protein of *Neisseria meningitidis*) was purchased from the Center of Genetic Engineering and Biotechnology of Havana. It is described in U.S. Pat. No. 5,286,484.

A conjugate between murine EGF and P64 protein was obtained using the glutaraldehyde conjugation method.

In order to demonstrate that the immunogenic preparation containing autologus EGF and P64 as carrier protein is capable of inducing autoimmunity, experiments were performed in Balb C mice.

Groups of animals were immunized subcutaneously with 10 µg/g of mu-EGF coupled to P64, twice, with a weekly frequency. In the first week the immunogenic preparation was prepared in a proportion 1:1 with Freund's complete adjuvant and in the second week in the same proportion with incomplete Freund's adjuvant. A control group was included of mice treated only with adjuvant.

Three weeks after the first immunization, serum was obtained and the titers against autologus EGF determined by an ELISA.

Costar plates were coated with mu-EGF at a concentration of 10 µg/ml in carbonate bicarbonate buffer (pH 9.6) and incubated overnight. After the plates were washed the samples were added in different dilutions. Incubation took place during one hour. Alkaline phosphatase anti-mouse antibody conjugate was added and incubated during one hour after which color was developed and optical density measured at 405 nm in an ELISA reader.

All animals immunized with the mu-EGF-P64 preparation developed antibody titers against the mu-EGF between 1:100 and 1:500 sera dilution. The control group did not show any antibody titer (FIG. 12).

EXAMPLE 15

STUDY OF IOR-T3 AND IOR-CEA1 AS CARRIER MOLECULES IN EGF VACCINE

IOR-T3 is a IgG2a monoclonal antibody that recognizes human T lymphocytes and IOR-CEA1 is a IgG1 monoclonal antibody that recognizes carcinoembryonic antigen. Both were tested as carrier protein in two vaccine preparations of EGF.

IOR-T3 and IOR-CEA1 were produced in the Center of Molecular Immunology of Havana.

Conjugates between hu-rec-EGF and both monoclonal antibodies were obtained using the glutaraldehyde conjugation method.

The study was performed in 3 chimpanzees (*Pan troglodytes*) which were submitted to a clinical veterinary examination including:

Physical examination,

Thorax X rays,

Blood tests.

Two of these monkeys were immunized either with hu-EFG coupled to IOR-T3 or with hu-EGF coupled to IOR-CEA1, with 4 doses of 50 µg of conjugated EGF. A control monkey was immunized with hu-EGF without coupling to any carrier protein, 4 doses of 50 µg. Immunizations were performed subcutaneously in weeks 1, 2, 3 and 4. Complete Freund's adjuvant was used in the first immunization and incomplete Freund's adjuvant in all others.

Blood was extracted from the animals on days 0, 14, 28, 42 and 56, and the antibody titers were determined in serum through an ELISA.

Costar plates were coated with hu-EGF at a concentration of 10 µg/ml in carbonate-bicarbonate buffer (pH 9.6), and incubated overnight. After the plates were washed the samples were added in different dilutions. Incubation took place during one hour. The alkaline phosphatase anti-human antibody conjugate was added and incubated during one hour, after which color was developed and optical density measured at 405 nm in an ELISA reader.

The monkeys immunized with hu-EGF coupled to IOR-T3 or to IOR-CEA1 developed antibody titers against hu-EGF, the control monkey did not. The developed titers are shown in FIG. 13.

EXAMPLE 16

IMMUNOGENICITY IN MONKEYS OF DIFFERENT VACCINE PREPARATIONS OF EGF USING AL(OH)$_3$ AS ADJUVANT

In order to test in non-human primates vaccine preparations in an adequate formulation to be used in future clinical assays, experiments were performed in Green Monkeys (*Cercopithecus aethiops*).

The study was performed in 6 primates, being submitted to a clinical veterinary examination including:

Physical examination,

Thorax X rays,

Blood tests.

The vaccine preparations tested were:

1. hu-rec-EGF coupled to tetanic toxoid (as described before), 50 µg of conjugated EGF per dose in 2 ml of final volume, adsorbed in Al(OH)$_3$ (2 mg per dose) for 3 hours at room temperature. Two monkeys were immunized with this preparation.

2. hu-rec-EGF coupled to IOR-T3 monoclonal antibody through the glutaraldehyde technique, 50 µg of conjugated EGF per dose in 2 ml of final volume, adsorbed in Al(OH)$_3$ (2 mg per dose) for 3 hours at room temperature. Two monkeys were immunized with this preparation.

3. hu-rec-EGF without coupling to any carrier protein as negative control in the experiment, 50 µg per dose, in 2 ml of final volume, adsorbed in Al(OH)$_3$ in the same way. Two monkeys were immunized with this preparation.

The immunization protocol was of two doses on days 0 and 14, and the product was administered subcutaneously.

Blood was extracted on days 0, 30 and 60 and serum tested for antibody titers against hu-EGF through an ELISA.

Costar plates were coated with hu-rec-EGF at a concentration of 10 µg/ml in carbonate-bicarbonate buffer (pH 9.6) and incubated overnight. After the plates were washed the samples were added in different dilutions. Incubation took place during one hour. The alkaline phosphatase anti-human antibody conjugate was added and incubated during one hour after which color was developed and optical density measured at 405 nm in an ELISA reader.

Monkeys immunized either with hu-EGF/TT or with hu-EGF/IOR-T3 developed antibody titers against hu-EGF as is shown in FIG. 14.

x axis: serial dilutions of the conjugate (from 0.1 mg/ml to 0.001 mg/ml);

y axis: optical density at 405 nm, measured in an ELISA plates reader.

Figure 1:
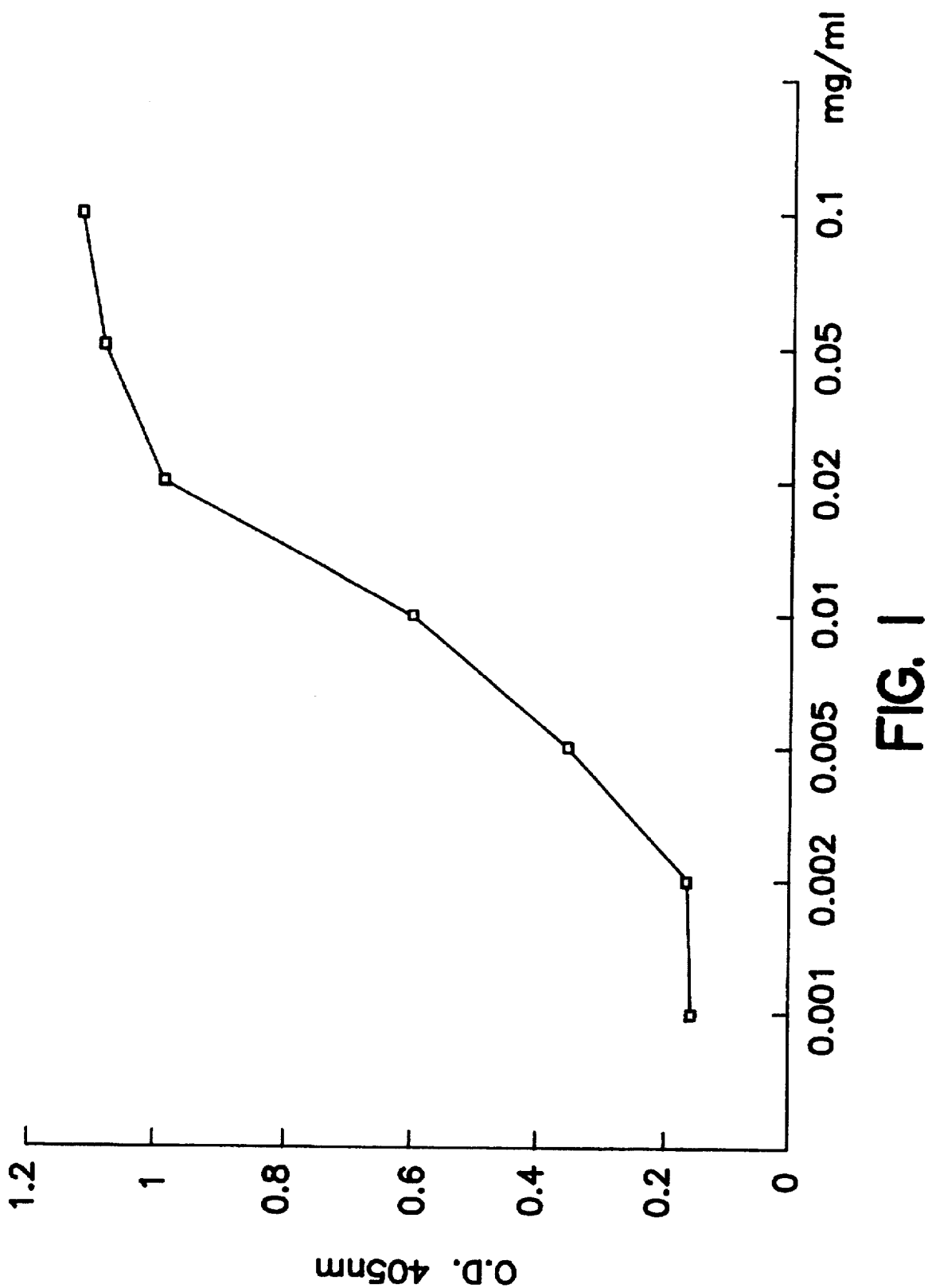
FIG. 1: ELISA assay for determination of conjugation efficiency between CTB and mu-EGF.
Figure 2:
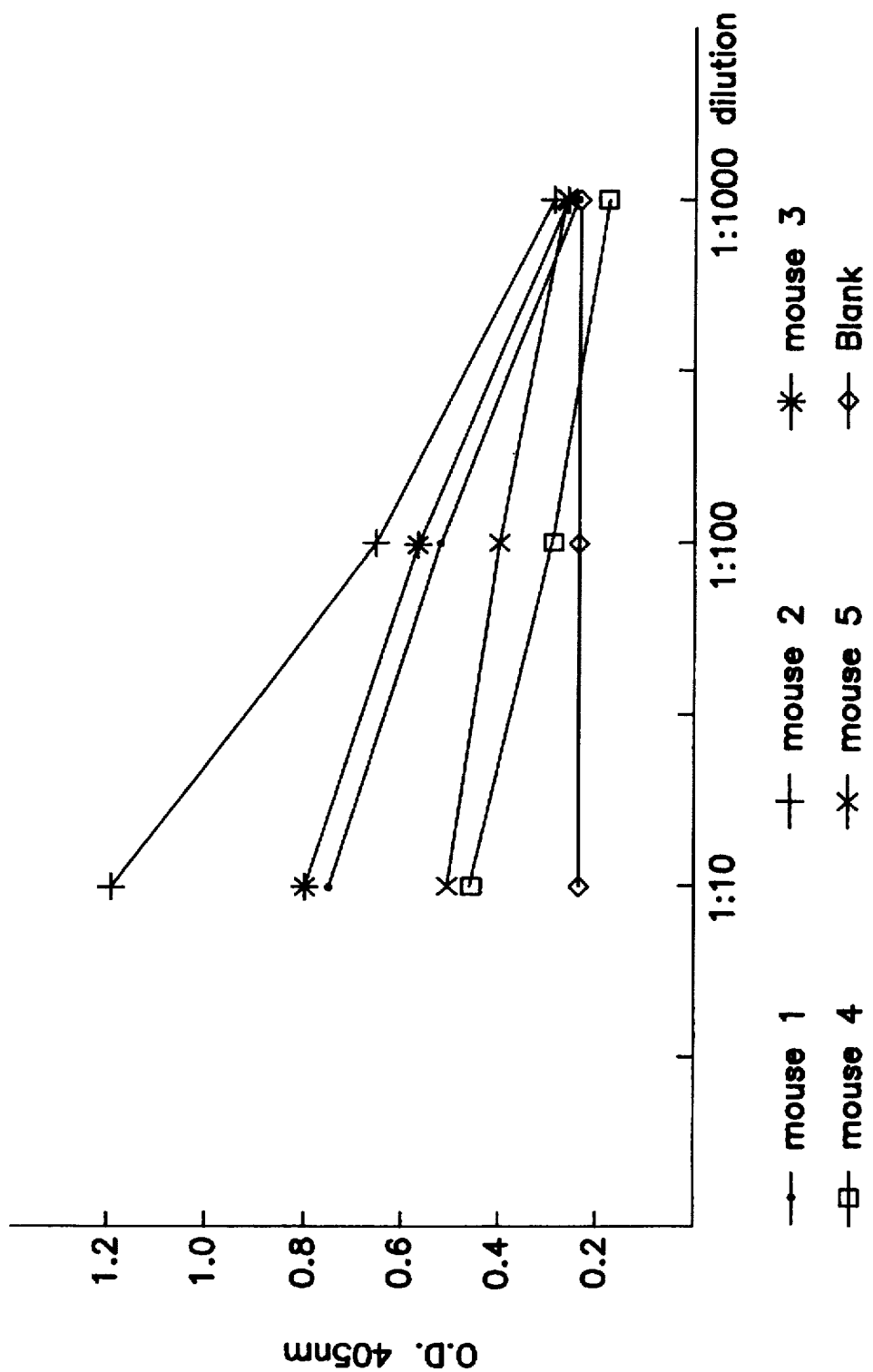

FIG. 2: ELISA assay for the determination of antibody titer against the mu-EGF in 5 mice immunized with the conjugated mu-EGF-CTB.

x axis: Antiserum dilutions (1:10, 1:100, 1:1000);

y axis: optical density at 405 nm, measured in an ELISA plate reader.

The curves represent the titer of 5 tested animals, compared with the same animals before immunization.

Figure 3:
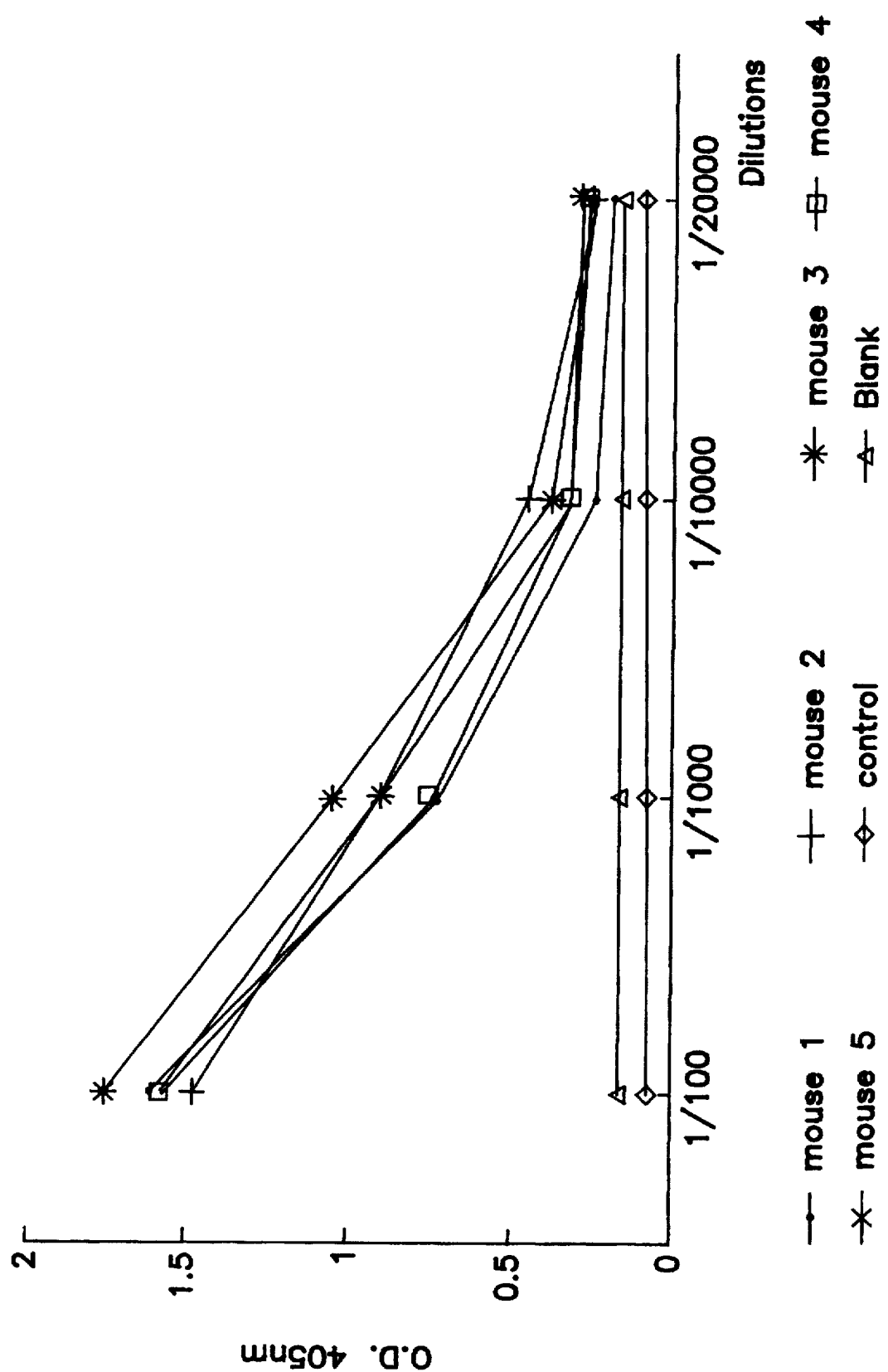

FIG. 3: ELISA assay for the determination of antibody titer against mu-EGF, in 5 mice immunized with hu-rec-EGF.

x axis: sera dilutions 1:100, 1:1000, 1:10000, 1:20000;

y axis: optical density at 405 nm.

Figure 4:
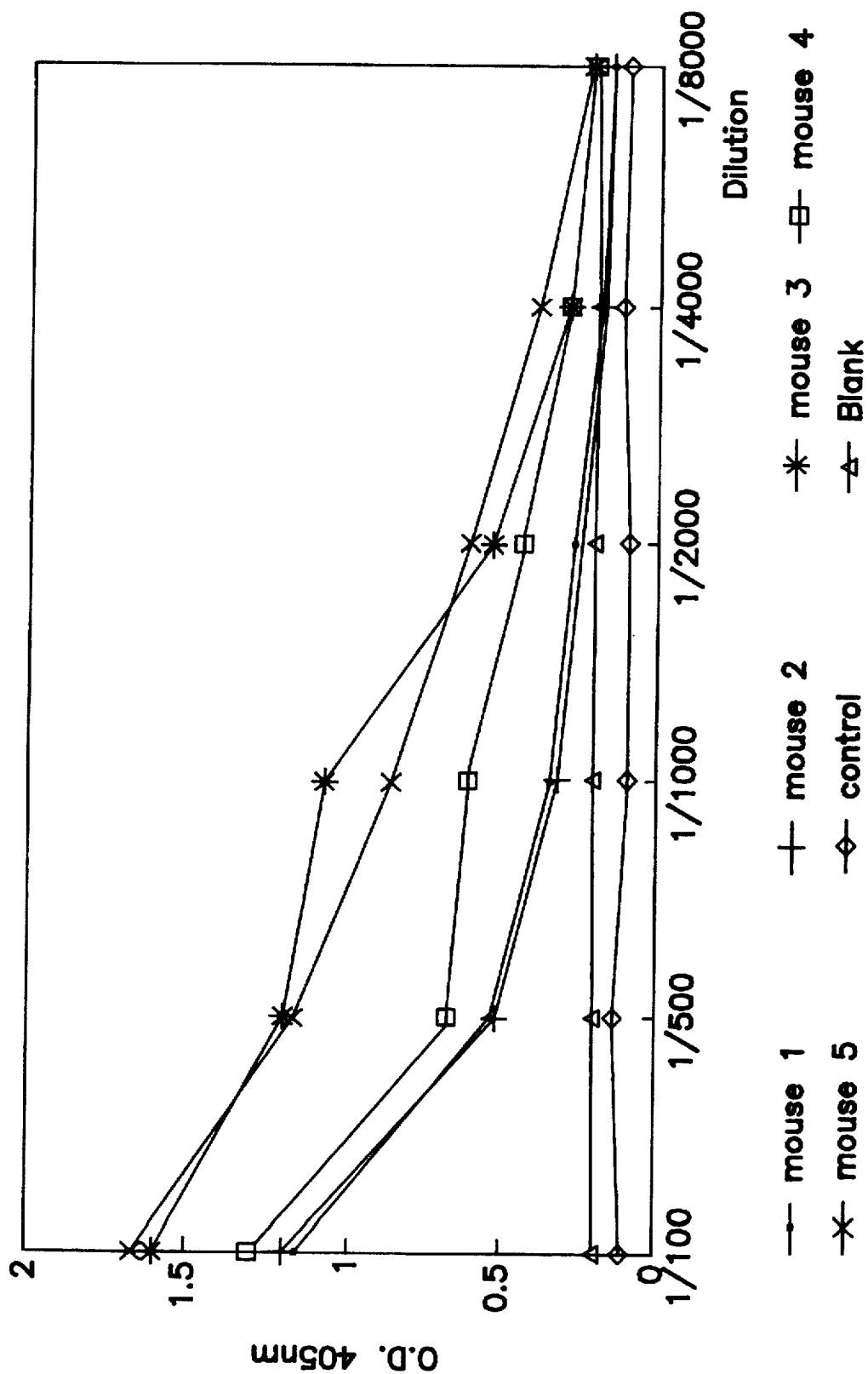

FIG. 4: ELISA assay for the determination of antibody titer against mu-EGF, in 5 mice immunized with hu-rec-EGF in aluminum hydroxide as adjuvant x axis: sera dilutions 1:100, 1:500, 1:1000, 1:2000, 1:4000, 1:8000;

y axis: optical density at 405 nm.

Figure 5:
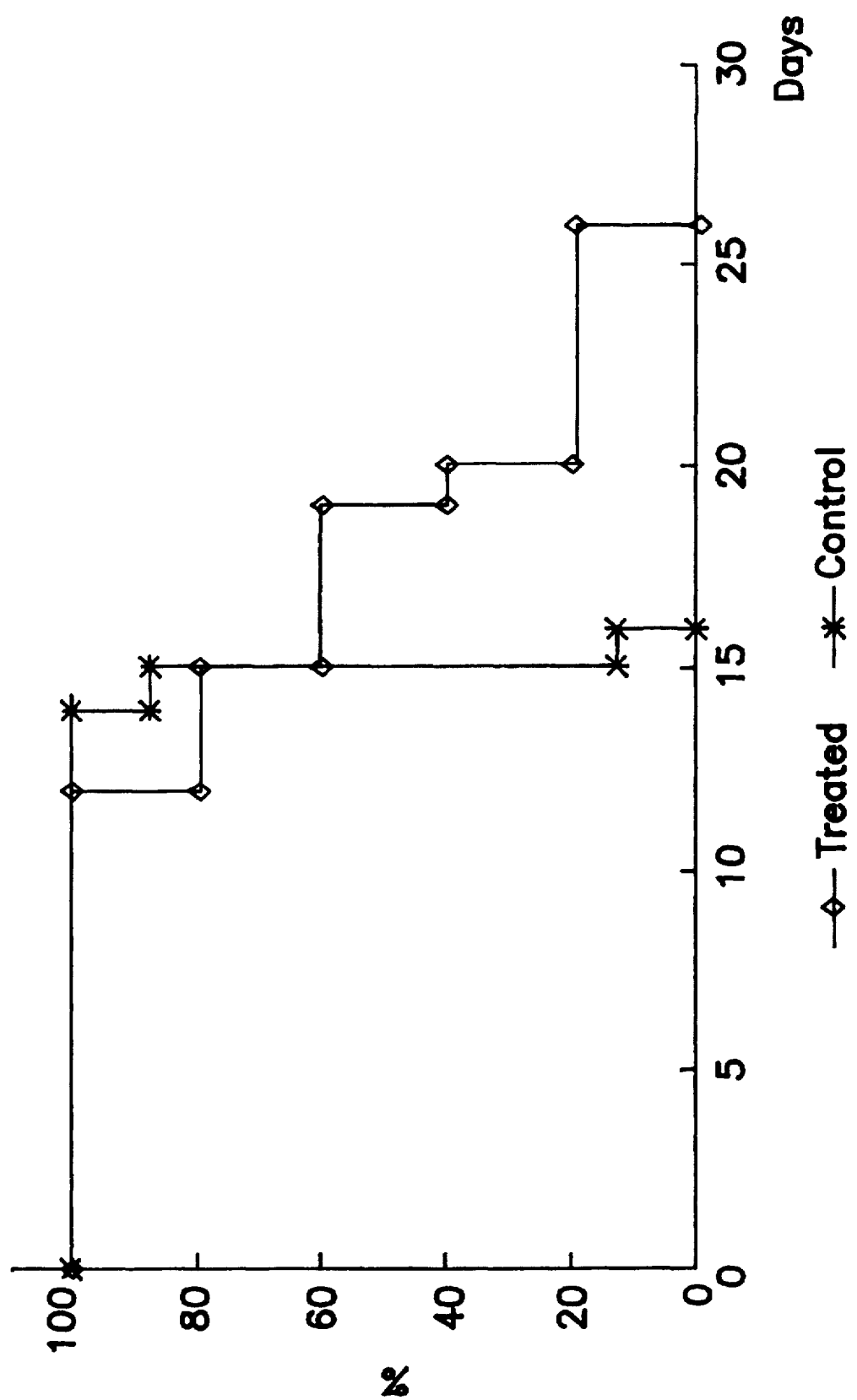

FIG. 5: Survival of animals immunized with mu EGF-CTB and subsequently inoculated with Ehrlich Ascites tumour, in comparison with control animals (non-immunized) and inoculated with the same tumor.

Figure 6B:
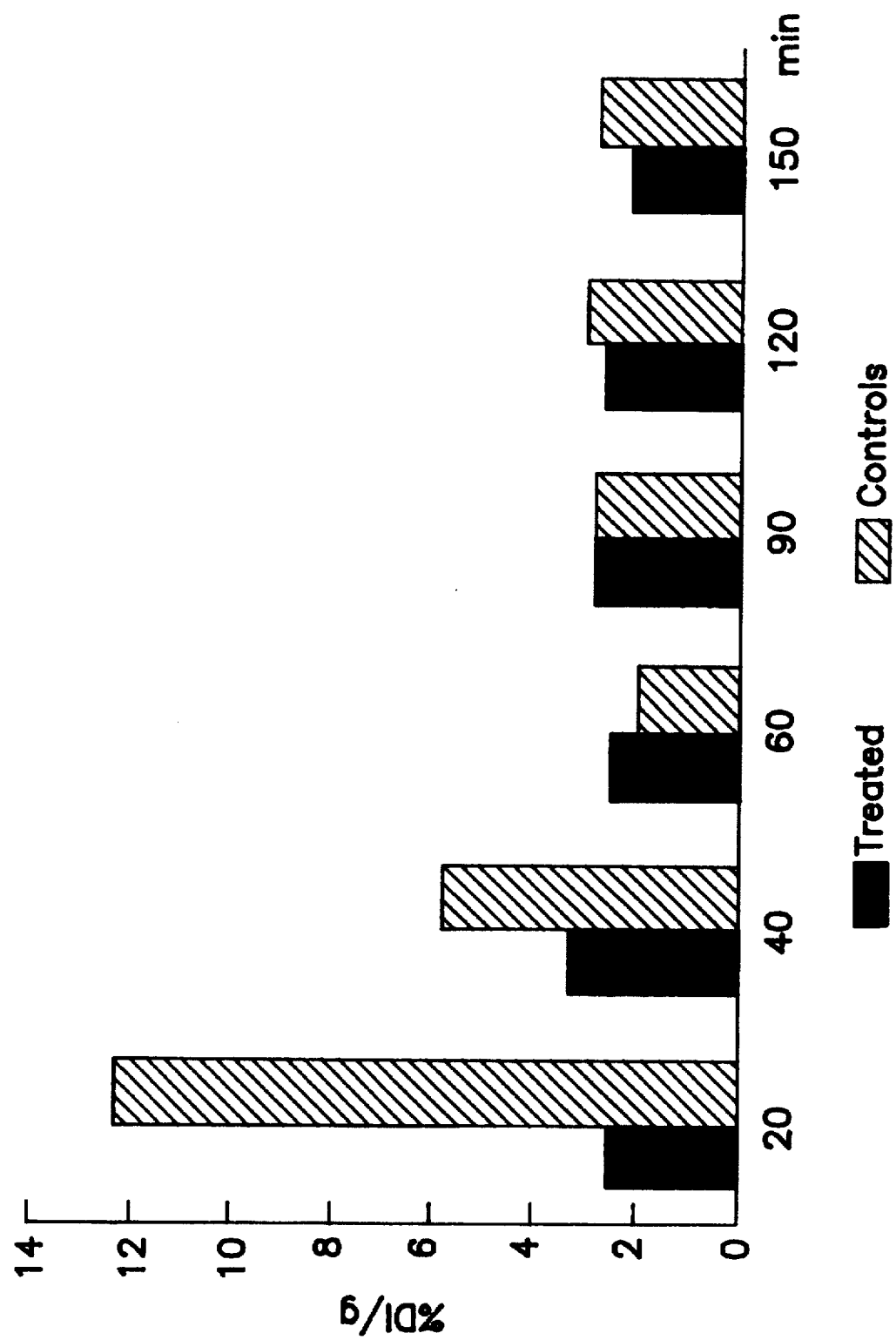

FIG. 6-a: Accumulation of $^{125}$I-EGF in liver of mice immunized with hu-rec-EGF in relation to non-immunized controls.

x axis: time in minutes;

y axis: percent of incorporated dose of radioactivity per gram of tissue.

FIG. 6-b: Accumulation of $^{125}$I-EGF in kidneys of mice immunized with hu-rec-EGF in relation to non-immunized controls.

x axis: time in minutes;

y axis: percent of incorporated dose of radioactivity per gram of tissue.

Figure 7:
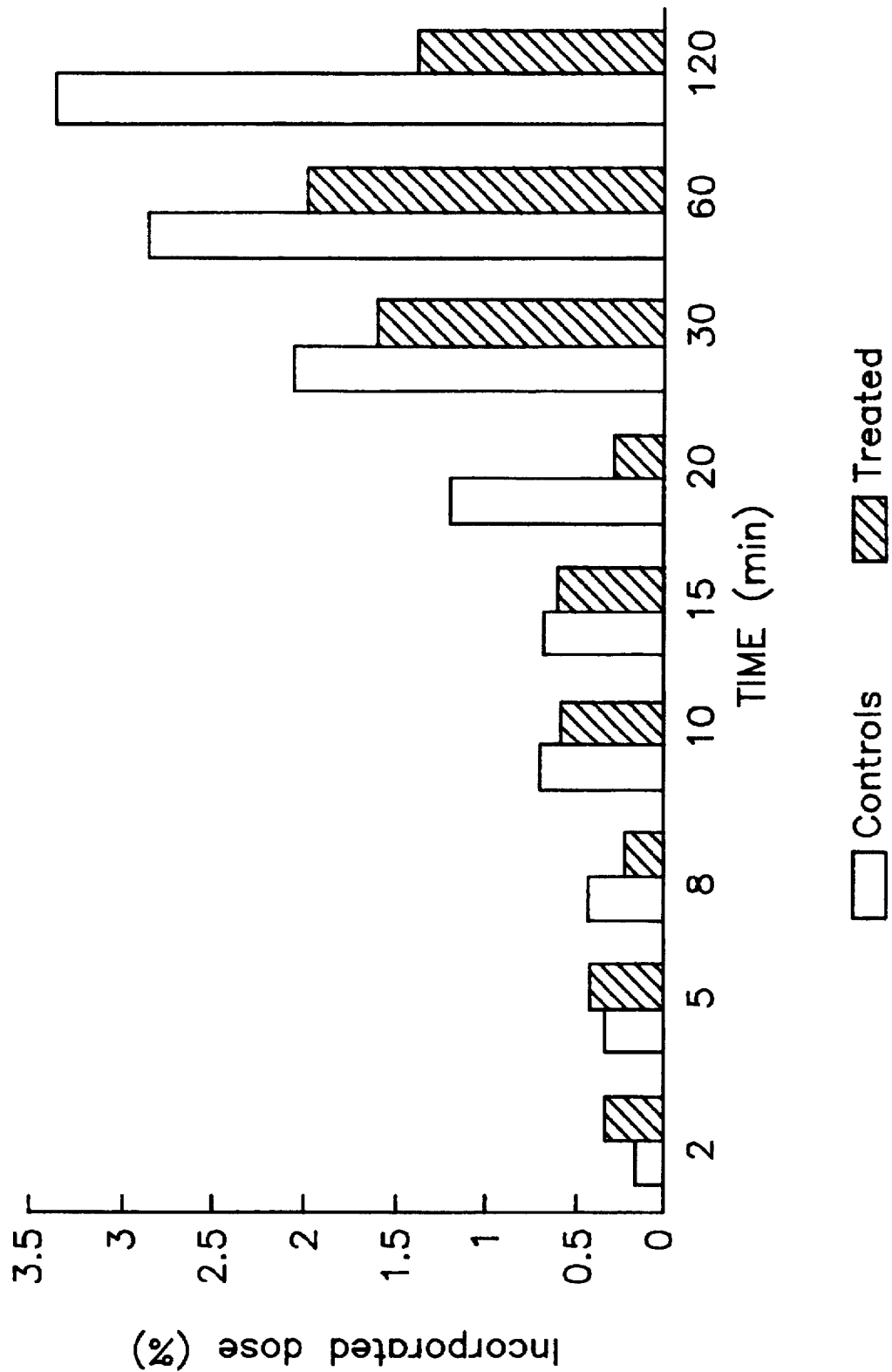

FIG. 7: Accumulation of $^{125}$I-mu-EGF in ascitic fluid of animals grafted with EAT, previously immunized with hu-rec-EGF.

Figure 8:
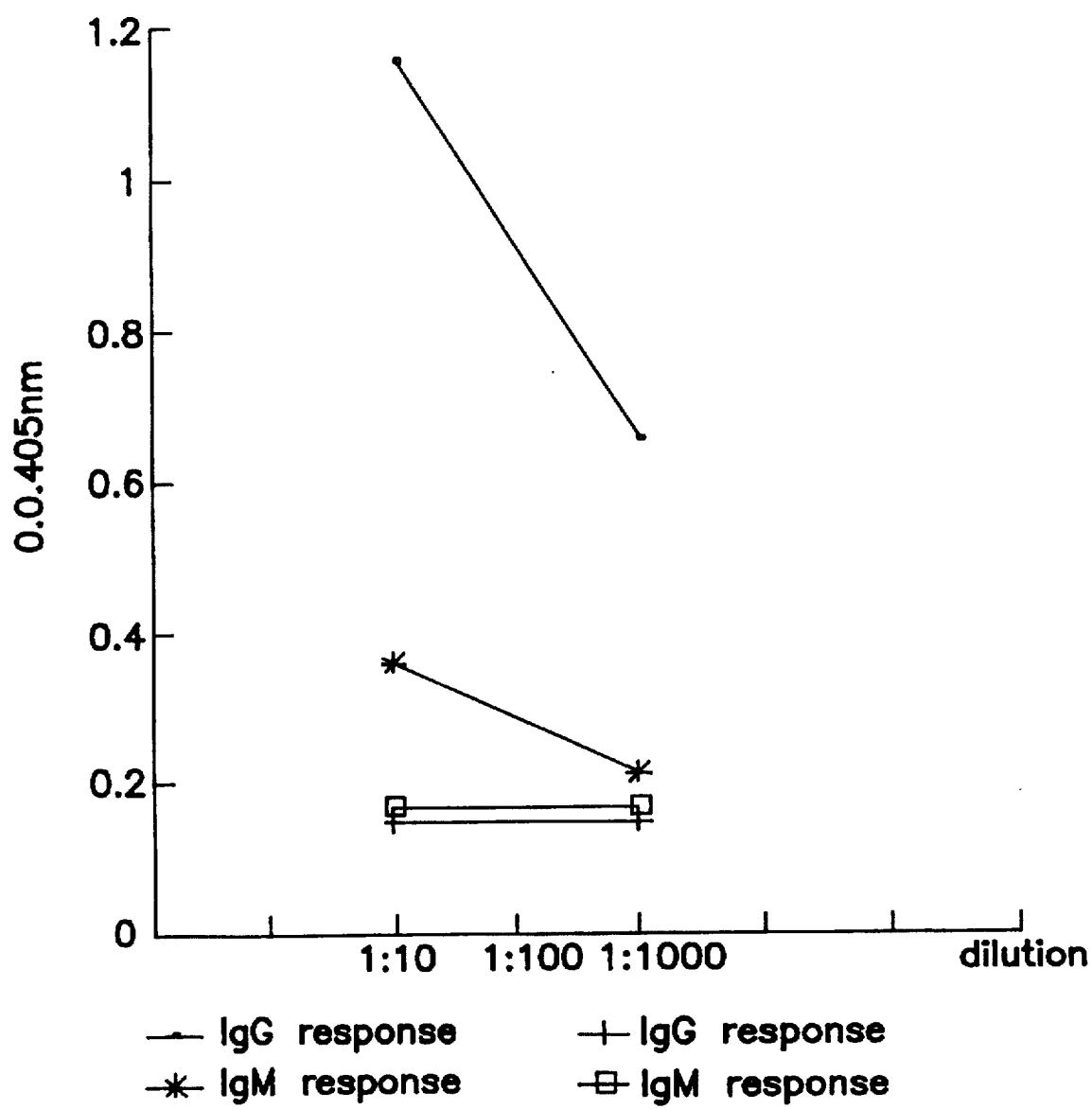

FIG. 8: ELISA assay for determination of IgG or IgM of the immune response in animals immunized with mu-EGF-CTB.

Figure 9:
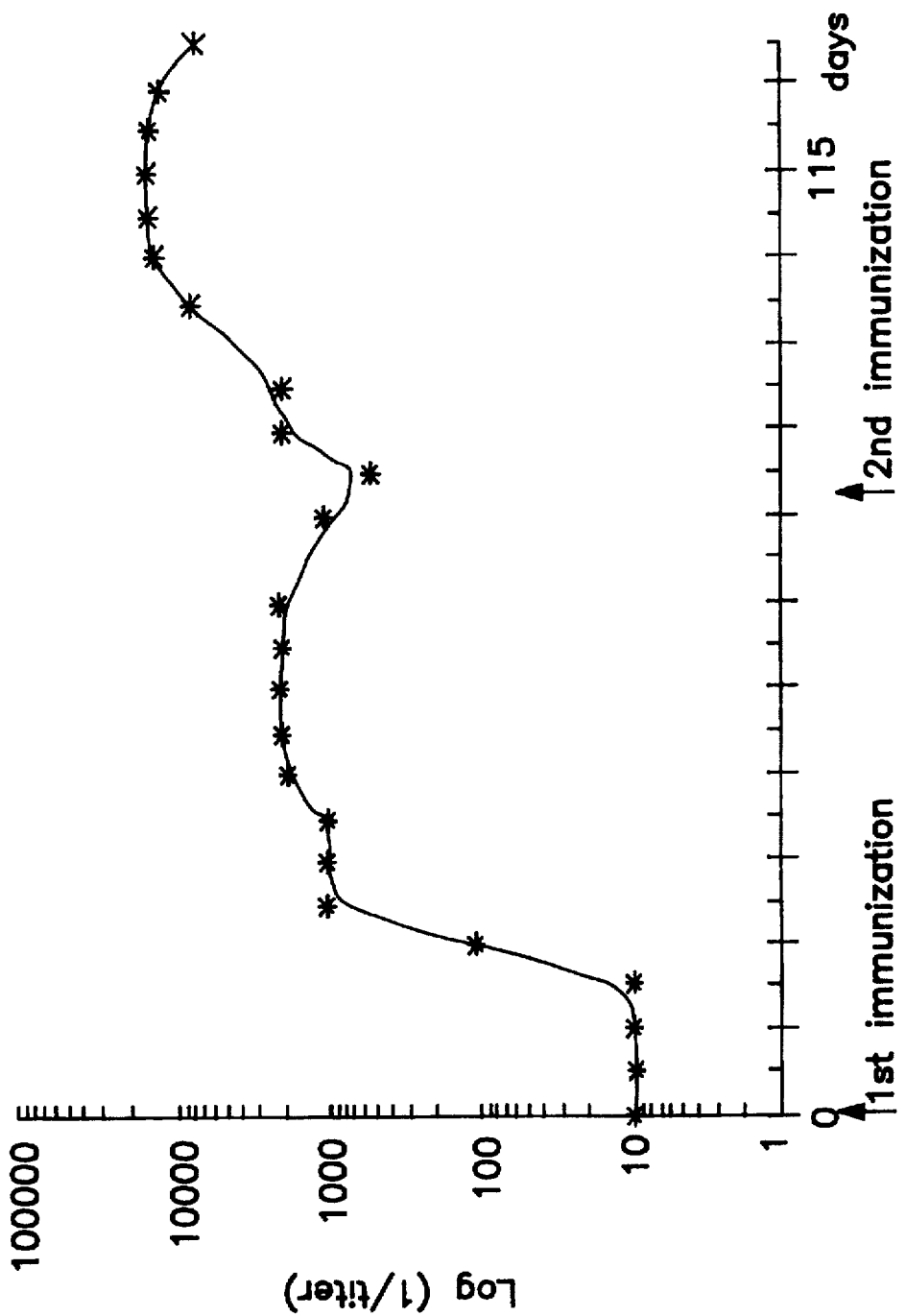

FIG. 9: Antibody response kinetics (IgG) against mu-EGF in animals immunized against hu-rec-EGF (Memory).

x axis: time (days);

y axis: Inverse logarithm of the antibody titer.(mean value).

Figure 10:
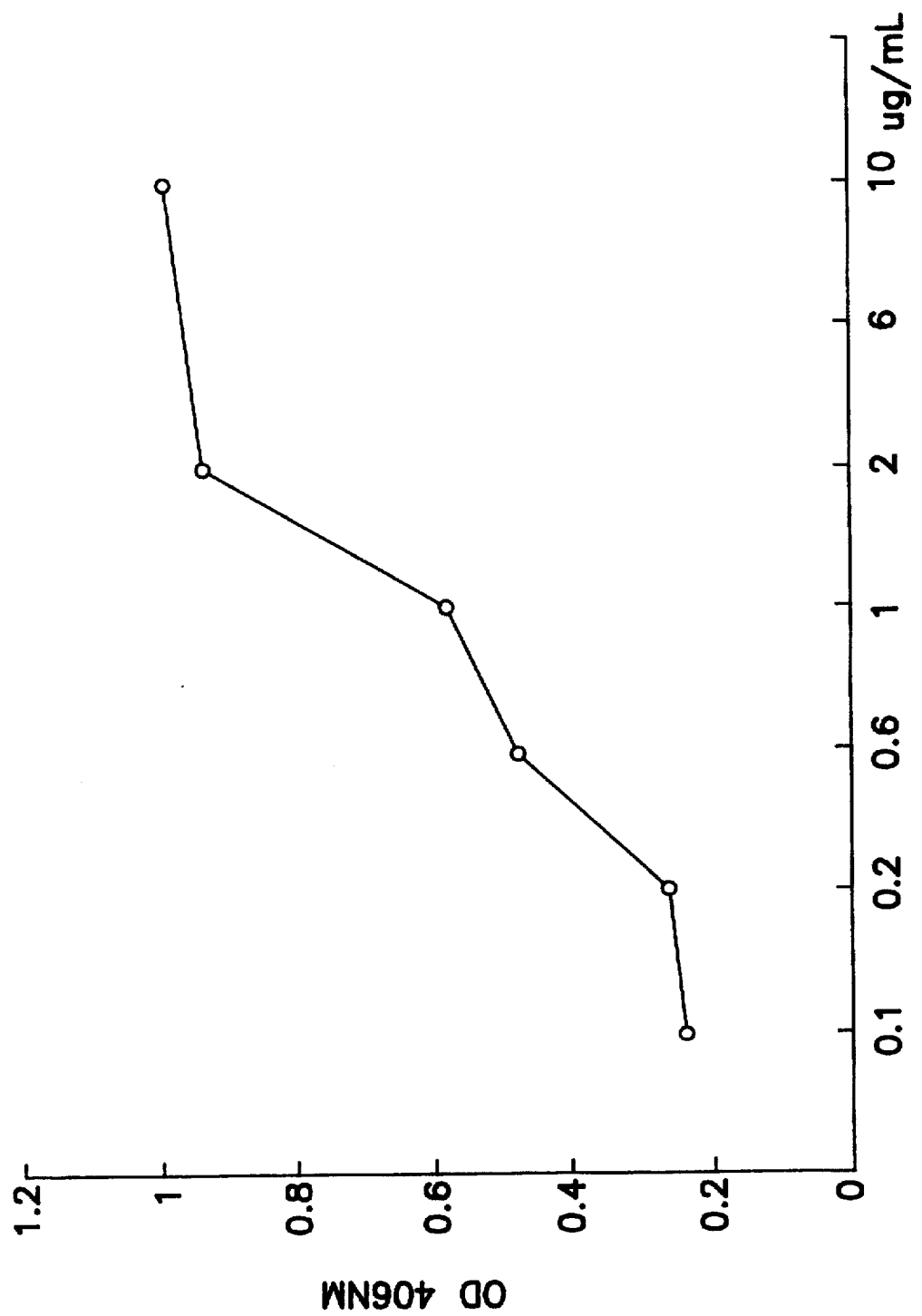

FIG. 10: ELISA assay for the determination of the efficiency of conjugation of Tetanic toxoid with hu-rec-EGF.

x axis: dilutions of conjugate;

y axis: optical density at 405 nm.

Figure 11:
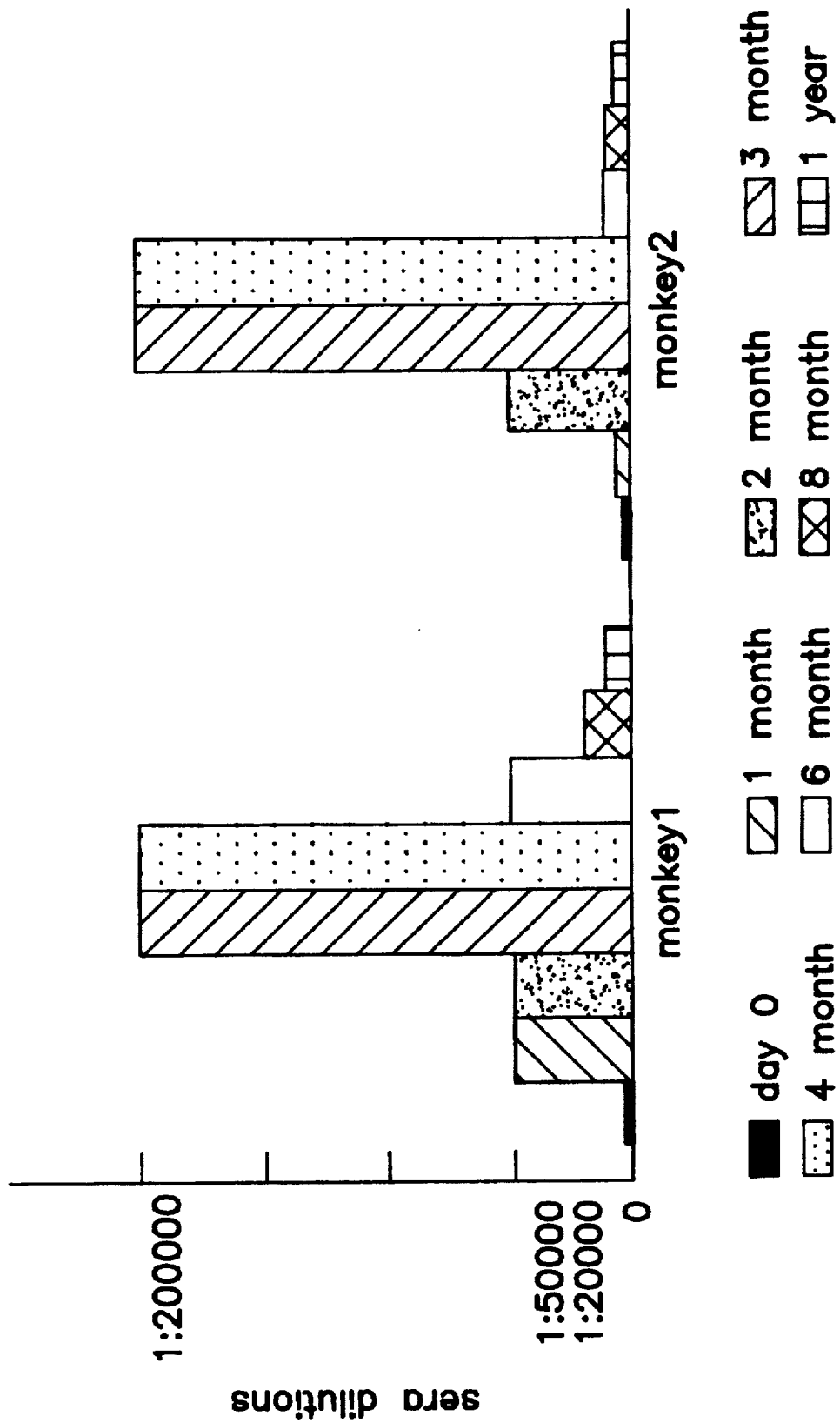

FIG. 11: antibody titer against hu-rec-EGF in non-human primates immunized with hu-rec-EGF, coupled to tetanic toxoid.

Figure 12:
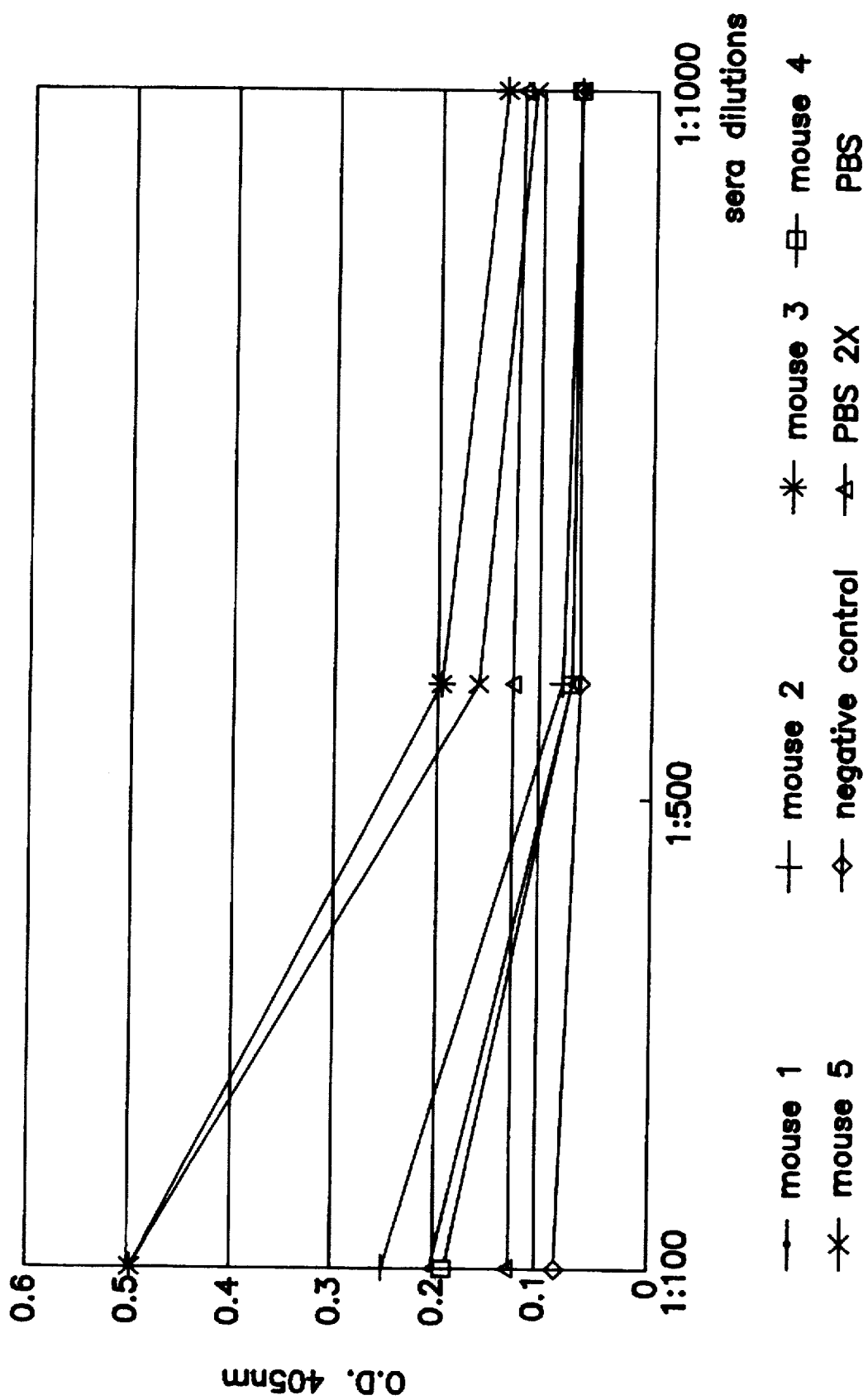

FIG. 12: Antibody titers against autologous EGF in mice immunized with murine EGF coupled to P64 carrier protein.

x-axis: mice sera dilutions;

y-axis: optical density at 405 nm.

Figure 13:
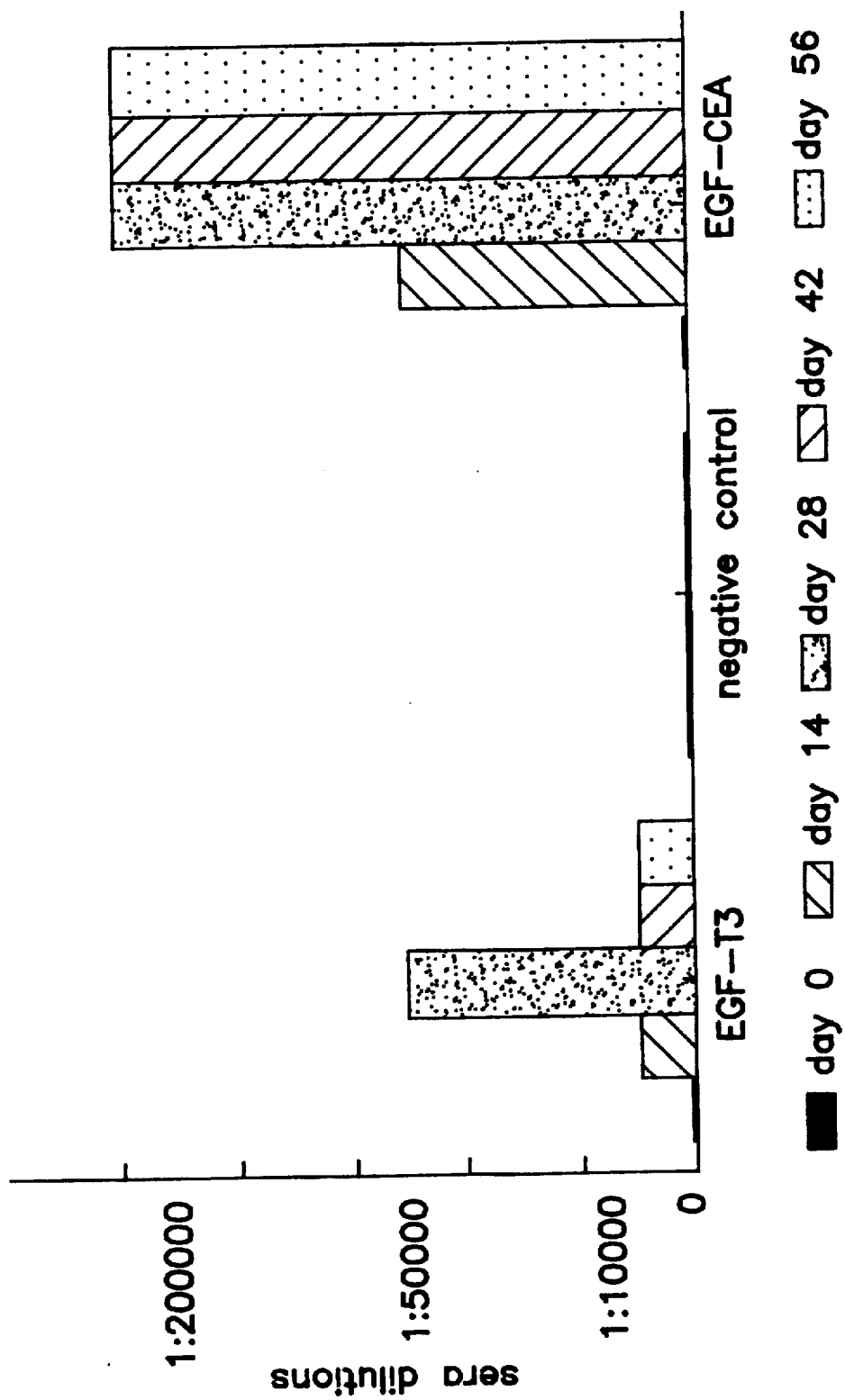

FIG. 13: Antibody titers against hu-rec-EGF in Chimpanzees (Pan troglodytes), one immunized with hu-rec-EGF coupled to IOR-T3 monoclonal antibody and the other with hu-rec-EGF coupled to CEA monoclonal antibody, using Freund's complete adjuvant. A negative control was included of a monkey immunized only with hu-rec-EGF in Freund's adjuvant.

Figure 14:
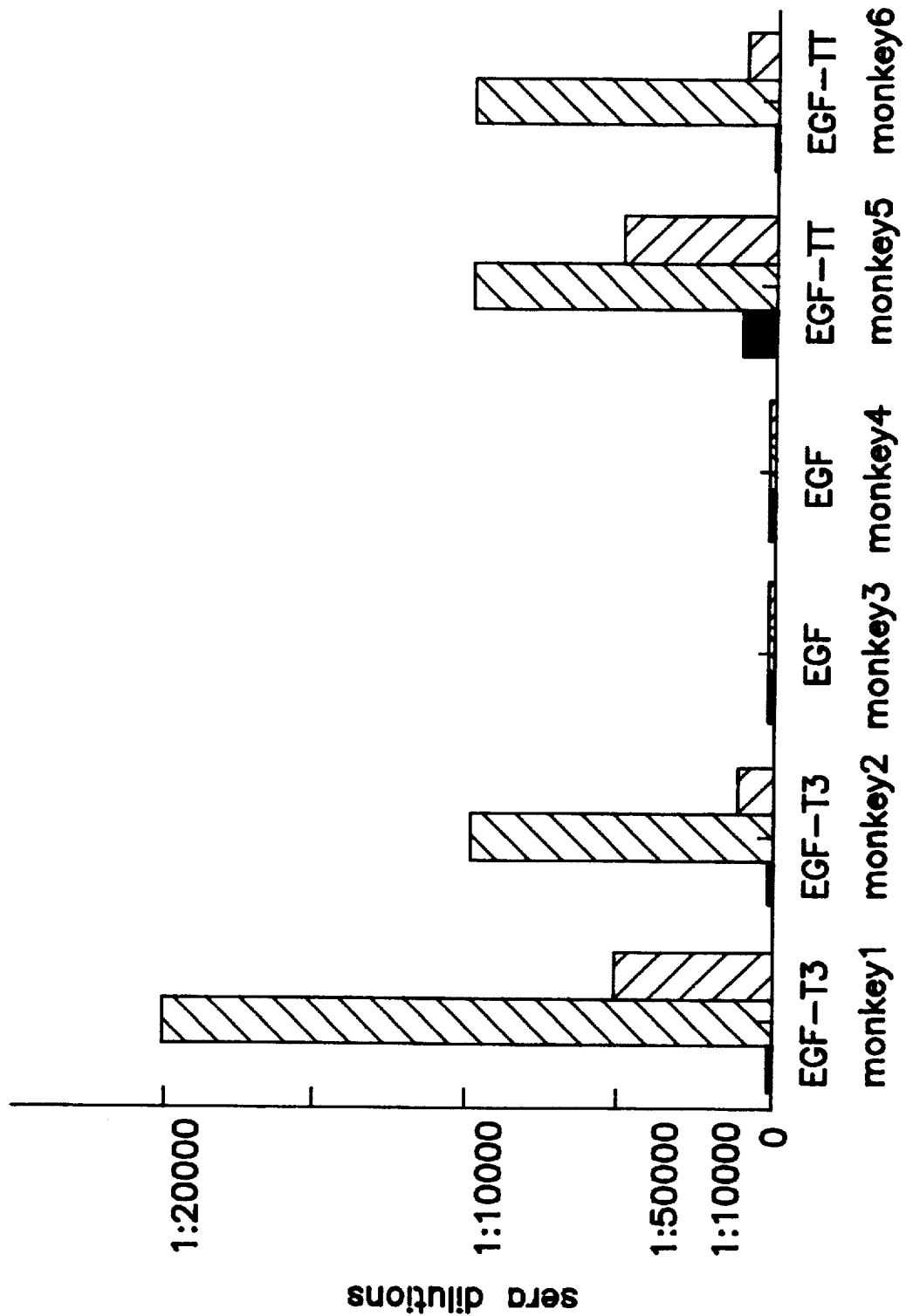

FIG. 14: Antibody titers against hu-rec-EGF in Green monkeys (Cercopithecus aethiops), immunized with hu-rec-EGF coupled to IOR-T3 monoclonal antibody and with hu-rec-EGF coupled to tetanic toxoid, using Al(OH)$_3$ as adjuvant. A negative control was included of two monkeys immunized with hu-rec-EGF in Al(OH)$_3$ adjuvant.

We claim:

1. A vaccine composition for administration to a human host for producing an autoimmune response against autologous Epidermal Growth Factor comprising Epidermal Growth Factor autologous to said host conjugated with a carrier protein and further comprising an adjuvant, the autologous Epidermal Growth Factor being an antigen for eliciting said autoimmune response.

2. A vaccine composition according to claim 1, wherein said Epidermal Growth Factor is human recombinant Epidermal Growth Factor.

3. A vaccine composition according to claim 1, wherein said carrier protein is cholera toxin B chain.

4. A vaccine composition according to claim 1, wherein said carrier protein is Tetanic Toxoid.

5. A vaccine composition according to claim 1, wherein said carrier protein is a monoclonal antibody.

6. A vaccine composition according to claim 1, wherein said carrier protein is a Neisseiria meningitidis outer membrane protein.

7. A vaccine composition according to claim 1, wherein said adjuvant is aluminum hydroxide.

8. A method of treating an Epidermal Growth Factor-dependent malignant disease, comprising administering a therapeutically effective dose of a vaccine composition according to claim 1.

9. A method according to claim 8, wherein said malignant disease is epidermoid carcinoma of the lung, glioblastoma multiforme, or head and neck epidermoid carcinoma.

10. A pharmaceutical composition for administration to a human host comprising an adjuvant and an amount, effective for treating an Epidermal Growth Factor-dependent malignant disease in said host, of Epidermal Growth Factor autologous to said host conjugated with a carrier protein.

11. A composition of claim 10, wherein said Epidermal Growth Factor is recombinant human Epidermal Growth Factor.

12. A composition of claim 11, wherein said carrier protein is cholera toxin B chain, Tetanic Toxoid, a monoclonal antibody or a Neisseiria meningitidis outer membrane protein.

13. A method of treating an Epidermal Growth Factor-dependent malignant disease in a human host in need thereof comprising administering to said host a composition of claim 10.

14. A method of claim 13, wherein said carrier protein is cholera toxin B chain, Tetanic Toxoid, a monoclonal antibody or a Neisseiria meningitidis outer membrane protein.

15. A method of claim 13, wherein the Epidermal Growth Factor in said composition is recombinant human Epidermal Growth Factor.

* * * * *

UNITED STATES PATENT AND TRADEMARK OFFICE
CERTIFICATE OF CORRECTION

PATENT NO  : 5,894,018
DATED      : April 13, 1999
INVENTOR(S): Davila et al.

It is certified that error appears in the above-identified patent and that said Letters Patent is hereby corrected as shown below:

On the Title Page (page 2) under "OTHER PUBLICATIONS" add --Article entitled: Evidence for the involvement of the submandibular gland epidermal growth factor in mouse mammary tumorigenesis. Authors: Hirohisa Kurachi, Shigeru Okamoto, and Takami Oka. Published in PNAS (USA), 82: 5940-5943 (1985).--;

On the Title Page (page 2) under "OTHER PUBLICATIONS" add --Article entitled: Satisfactory and Unsatisfactory Tumor Models: Factors Influencing the Selection of a Tumor Model for Experimental Evaluation. Author: Dietmar W. Siemann. Published in Rodent Tumor Models in Experimental Cancer Therapy, ed. Kallman, pp.12-15 (Pergamon Press, NY, 1987).--;

On the Title Page (page 2) under "OTHER PUBLICATIONS" add --Article entitled: Epidermal Growth Factor Induces Rapid Tyrosine Phosphorylation of Proteins in A431 Human Tumor Cells. Authors: Troy Hunter and Jonathan A. Cooper. Published in Cell, 24: 741-752 (1981).--;

On the Title Page (page 2) under "OTHER PUBLICATIONS" add --Article entitled: Growth Factors: Mechanism of Action and Relation to Oncogenes. Authors: Carl-Henrik Heldin and Bengt Westermark. Published in Cell, 37: 9-20 (1984).--;

In column 8, line 43, delete "125I EGF" and insert --$^{125}$I-EGF--.

Signed and Sealed this

Seventeenth Day of October, 2000

*Attest:*

Q. TODD DICKINSON

*Attesting Officer*  *Director of Patents and Trademarks*